(12) United States Patent
Madhani et al.

(10) Patent No.: US 10,335,530 B2
(45) Date of Patent: Jul. 2, 2019

(54) LUNG ASSIST DEVICE WITH OSCILLATING FIBER BUNDLE

(71) Applicant: University of Pittsburgh—Of the Commonwealth System of Higher Education, Pittsburgh, PA (US)

(72) Inventors: Shalv Madhani, Pittsburgh, PA (US); Brian Joseph Frankowski, Imperial, PA (US); William J. Federspiel, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 318 days.

(21) Appl. No.: 15/288,111

(22) Filed: Oct. 7, 2016

(65) Prior Publication Data
US 2017/0100531 A1 Apr. 13, 2017

Related U.S. Application Data

(60) Provisional application No. 62/238,364, filed on Oct. 7, 2015.

(51) Int. Cl.
*A61M 1/16* (2006.01)
*B01D 63/02* (2006.01)
*A61M 1/26* (2006.01)

(52) U.S. Cl.
CPC ........ *A61M 1/1625* (2014.02); *A61M 1/1649* (2014.02); *A61M 1/1698* (2013.01);
(Continued)

(58) Field of Classification Search
CPC .............. A61M 1/1625; A61M 1/1649; A61M 1/1698; A61M 1/26; A61M 2202/0208;
(Continued)

(56) References Cited

U.S. PATENT DOCUMENTS

| 6,428,747 B1 | 8/2002 | Dueri |
| 6,503,451 B2 * | 1/2003 | Ikeda ................. A61M 1/1698 422/45 |
| 2007/0020142 A1 * | 1/2007 | Federspiel .......... A61M 1/1698 422/45 |

FOREIGN PATENT DOCUMENTS

| WO | WO2006031858 A1 | 3/2006 |
| WO | WO2014085620 A1 | 6/2014 |

OTHER PUBLICATIONS

Koller T, Hawrylenko A: Contribution to the in vitro testing of pumps for extracorporeal circulation J Thorac Cardiovasc Surg 54: 22-29, (1967).

(Continued)

*Primary Examiner* — Benjamin J Klein
(74) *Attorney, Agent, or Firm* — Bartony & Associates, LLC

(57) ABSTRACT

An extracorporeal system for lung assist includes a system housing, which includes a blood flow inlet and a blood flow outlet and a fiber bundle housing movably positioned within the system housing. The fiber bundle housing includes a gas inlet and a gas outlet. A fiber bundle is in operative connection with the fiber bundle housing. The fiber bundle includes a plurality of hollow gas permeable fibers, wherein lumens of the plurality of hollow gas fibers are in fluid connection with the gas inlet at a first end thereof and in fluid connection with the gas outlet as a second end thereof. The system further includes an actuator to impart oscillatory motion to the fiber bundle housing and thereby to the fiber bundle.

22 Claims, 8 Drawing Sheets

(52) U.S. Cl.
CPC ............... *A61M 1/26* (2013.01); *B01D 63/02* (2013.01); *A61M 2202/0208* (2013.01); *A61M 2202/0225* (2013.01); *A61M 2205/3334* (2013.01); *B01D 2311/2661* (2013.01); *B01D 2315/04* (2013.01)

(58) Field of Classification Search
CPC .. A61M 2202/0225; A61M 2205/3334; B01D 2315/04
See application file for complete search history.

(56) References Cited

OTHER PUBLICATIONS

ISO 7199:2009 Cardiovascular implants and artificial organs—Blood-gas exchangers (oxygenators):, 2009; ASTM F1841-97 Standard Practice for Assessment of Hemolysis in Continuous Flow Blood Pumps:, 2013.

Wu, Z. J. et al., Progress toward an ambulatory pump-lung. The Journal of thoracic and cardiovascular surgery, 130(4), (2005), 973-978.

Zhang, T. et al., A novel wearable pump-lung device: In vitro and acute in vivo study. The Journal of Heart and Lung Transplantation, 31(1), (2012), 101-105.

Wu, Z. J. et al., Thirty-day in-vivo performance of a wearable artificial pump-lung for ambulatory respiratory support. The Annals of thoracic surgery, 93(1), (2012), 274-281.

Schewe, R. E. et al. In-parallel attachment of a low-resistance compliant thoracic artificial lung under rest and simulated exercise. The Annals of thoracic surgery, 94(5), (2012), 1688-1694.

Qamar, Adnan, Robinson Seda, and Joseph L. Bull. "Pulsatile flow past an oscillating cylinder." Physics of Fluids (1994-present) 23.4 (2011): 041903.

* cited by examiner

LUNG ASSIST DEVICE WITH OSCILLATING FIBER BUNDLE

CROSS-REFERENCE TO RELATED APPLICATIONS

This application claims benefit of U.S. Provisional Patent Application Ser. No. 62/238,364, filed Oct. 7, 2015, the disclosure of which is incorporated herein by reference.

GOVERNMENTAL INTEREST

This invention was made with government support under grant no. NHLBI 5R01HL117637 awarded by the National Institutes of Health. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Acute and chronic lung diseases are prevalent in the United States, being the third leading cause of death in the United States. Mortality associated with acute respiratory distress syndrome or ARDS remains between 40% and 60%. The conventional interventions include mechanical ventilation (MV) and extracorporeal membrane oxygenation (ECMO). Those treatments, while effective in the short term (for example, over a period of 1 to 2 weeks) can be harmful long term. In that regard, it is challenging to ambulate and rehabilitate while on MV or ECMO. The only viable treatment currently available is lung transplant. However, the wait times on the transplant list can be several months. Thus, there is a clinical need for a long-term ambulatory support device that can replace MV and ECMO (for example, to minimize wait list mortality).

SUMMARY

In one aspect, an extracorporeal system for lung assist includes a system housing, which includes a blood flow inlet and a blood flow outlet and a fiber bundle housing movably positioned within the system housing. The fiber bundle housing includes a gas inlet and a gas outlet. A fiber bundle is in operative connection with the fiber bundle housing. The fiber bundle includes a plurality of hollow gas permeable fibers, wherein lumens of the plurality of hollow gas fibers are in fluid connection with the gas inlet at a first end thereof and in fluid connection with the gas outlet as a second end thereof. The system further includes an actuator to impart oscillatory motion to the fiber bundle housing and thereby to the fiber bundle. Blood may, for example, be sealed/blocked from flowing to the gas inlet and the gas outlet. And sweep gas from the gas inlet and gas outlet may be sealed/blocked from flowing into the blood.

The plurality of hollow gas permeable fibers may, for example, be adapted to permit diffusion of gas between blood and an interior of the plurality of hollow gas permeable fibers. In a number of embodiments, the plurality of hollow gas permeable fibers are positioned such that blood flows around the plurality of hollow gas permeable fibers when flowing through the fiber bundle, and the plurality of hollow gas permeable fibers extends generally perpendicular to the direction of bulk flow of blood through the fiber bundle. In a number of embodiments, the system is a paracorporeal system.

The plurality of hollow gas permeable fibers may, for example, include a plurality of layers of fiber fabric, wherein each of the plurality of layers of fiber fabric includes hollow gas permeable fibers. In a number of embodiments, adjacent layers of fiber fabric are rotated relative to each other such that the orientation of the plurality of hollow gas permeable fibers in adjacent layers of fiber fabric are of a different orientation. The plurality of hollow gas permeable fibers may, for example, be formed in a generally cylindrical fiber bundle.

In a number of embodiments, the mean velocity of blood through the fiber bundle is in the range of approximately 0.6 to 7 cm/sec or 0.6 to 1.8 cm/sec for a high flow oxygenation device and in the range of approximately 0.08 to 1.2 cm/sec or 0.08 to 0.3 cm/sec for a low-flow $CO_2$ removal device. In a number of embodiment, a cross-sectional area of the fiber bundle is no more than 0.6 $m^2$. The system may, for example, be adapted to deliver flows in the range of approximately 2 to 4 liters per minute for a high flow oxygenation device and flows in the range of approximately 250 to 400 ml/min for a low-flow $CO_2$ removal device. The flow/flow rate may, for example, be adjustable.

The oscillatory motion of the fiber bundle may, for example, include at least one of linear oscillatory motion or rotational/torsional oscillatory motion. In a number of embodiments, a product of Womersley number and the Schmidt number is at least 10.

In another aspect, a method of providing lung assist includes providing a system including a system housing, the system housing including a blood flow inlet and a blood flow outlet in fluid connection with a patient's vasculature, a fiber bundle housing movably positioned within the system housing, the fiber bundle housing including a gas inlet and a gas outlet, and a fiber bundle in operative connection with the fiber bundle housing, the fiber bundle including a plurality of hollow gas permeable fibers, wherein lumens of the plurality of hollow gas fibers are in fluid connection with the gas inlet at a first end thereof and in fluid connection with the gas outlet as a second end thereof; and imparting oscillatory motion to the fiber bundle housing and thereby to the fiber bundle.

In a further aspect, an extracorporeal system for lung assist includes a housing, a fiber bundle including a plurality of hollow gas permeable fibers, and an actuator to impart oscillatory motion to the fiber bundle.

In still a further aspect, a method of providing lung assist includes providing a system including a housing and a fiber bundle movably positioned within the housing, the fiber bundle including a plurality of hollow gas permeable fibers; and imparting oscillatory motion to the fiber bundle.

Although the devices, systems and methods hereof are discussed in the representative examples hereof in connection with oxygenation of blood and/or removal of carbon dioxide from blood, the devices, systems and method hereof may be used generally to provide gas exchange between a liquid and a sweep gas via hollow gas permeable fibers.

The present devices, systems, and methods, along with the attributes and attendant advantages thereof, will best be appreciated and understood in view of the following detailed description taken in conjunction with the accompanying drawings.

DETAILED DESCRIPTION

Figure 1A:
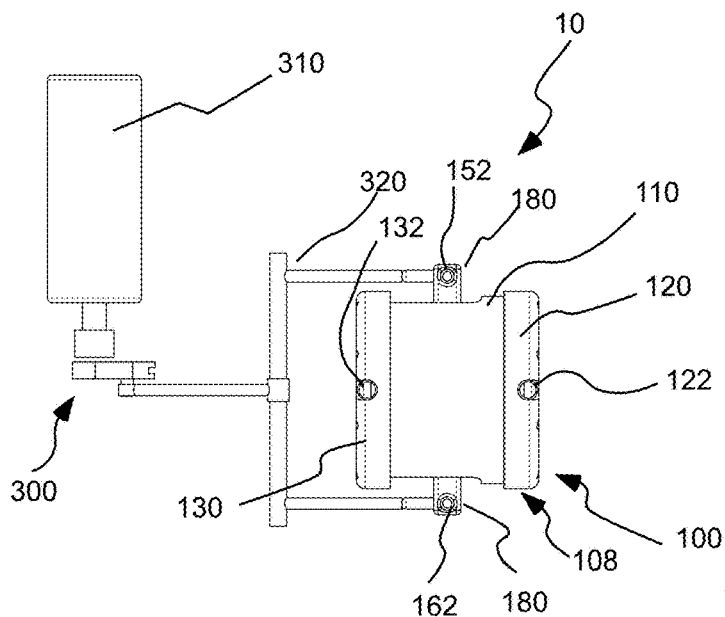
FIG. 1A illustrates a top plan view of an embodiment of a Paracorporeal Ambulatory Assist Lung or PAAL system hereof including a drive system and a lung assist device.
Figure 1B:
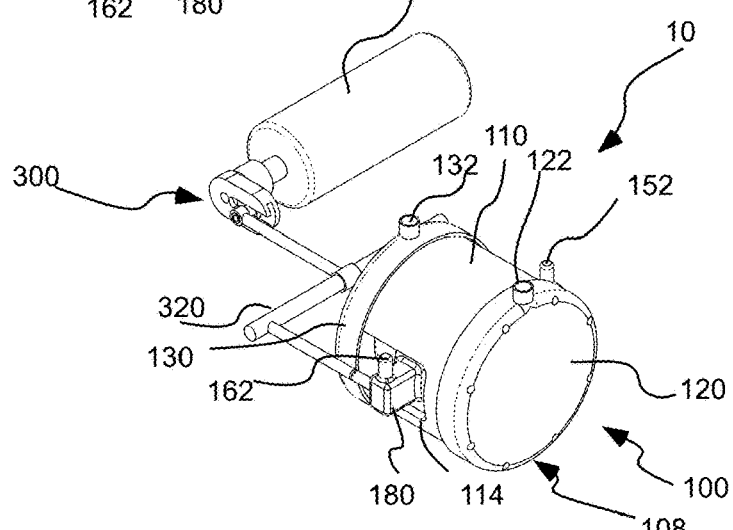
FIG. 1B illustrates a perspective view of the system of FIG. 1A.
Figure 1C:
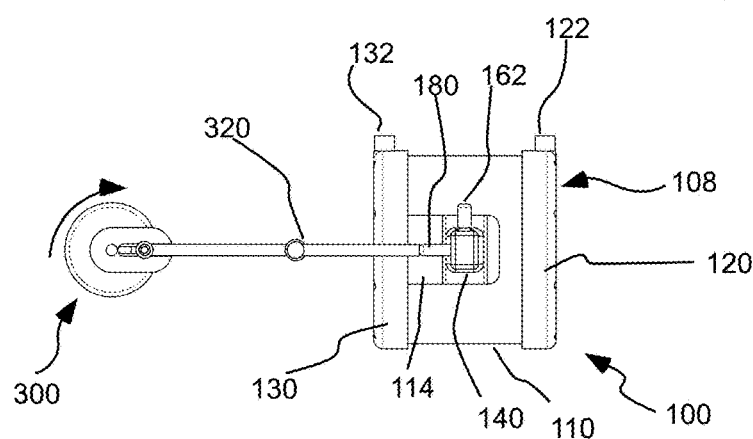
FIG. 1C illustrates a side view of the system of FIG. 1A.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "fiber bundle" includes a plurality of such fiber bundles and equivalents thereof known to those skilled in the art, and so forth, and reference to "the fiber bundle" is a reference to one or more such fiber bundles and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

To address the need for a relatively long-term ambulatory support device or system that can replace MV and ECMO and reduce or minimize wait list mortality, devices, systems and method hereof provide a "bridge" to recovery or transplant artificial lung devices. One goal for such devices is to allow for ambulation while providing long-term (for example, 1-3 month) support. In accomplishing this and other goals, it is desirable to reduce or minimize device size and HFM surface area. HFM surface area can be reduced by increasing gas exchange efficiency. Previous methodologies to achieve increased gas exchange efficiency have included, for example, continuously rotating a fiber bundle. Such fiber bundles may, for example, be formed from hollow fiber membranes or HFM. We have found, however, that significant drag within the fiber bundle results in very little disruption of boundary layers which form on fibers within the fiber bundle upon rotation of the fiber bundler at rates of rotation which do not cause significant blood hemolysis, and any increase in gas exchange efficiency is modest. Gas exchange efficiency has also been increased by creating a mixing effect through use of, for example, impellers, which gently disrupt the boundary layer that forms on the fiber surface. Increasing rotation speed of such impellers increases gas exchange efficiency, but results in an increase in induced hemolysis. $CO_2$ removal and oxygen enhancement is thus limited in such devices by an acceptable threshold of hemolysis.

In a number of representative embodiments hereof, perturbations are directly applied to fibers or hollow fiber membranes of a fiber bundle by oscillating the hollow fiber membranes in, for example, blood to locally disrupt the concentration boundary layer adjacent to each fiber. A goal of oscillating the HFM/fiber bundle is to decouple gas exchange enhancement and hemolysis. In that regard, a system 10 hereof including a lung assist device 100 (sometime referred to as an Oscillating Fiber Paracorporeal Ambulatory Assist Lung or OF-PAAL device) hereof, as illustrated, for example, in FIGS. 1A through 3) was designed to have a low level of hemolysis while proving significant gas exchange enhancement.

In a number of representative studied embodiments, device 100 includes a housing 108. In the illustrated embodiment, housing 108 includes a first or central section 110, a second or blood outlet section 120, and a third or blood inlet section 130. Second section 120 includes a blood inlet or inlet port 122 via which blood (or other fluid to/from which a gas is to be exchanged) is introduced to the interior of housing 108. Third section 130 includes a blood outlet or outlet port 132 via which blood (or other fluid to/from which gas is to be exchanged) exits the interior of housing 108. Blood inlet port 122 and blood outlet port 132 may be placed in fluid connection with the circulator system of a patient as known in the art.

Figure 2D:
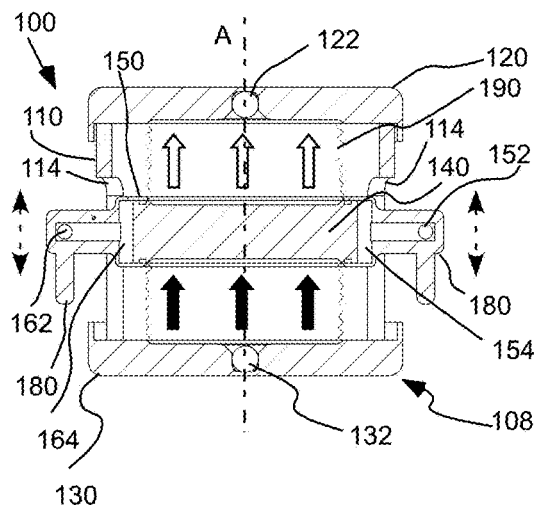
FIG. 2D illustrates a cross-sectional view (section B-B as illustrated in FIG. 2B) of the lung assist device.
Figure 2B:
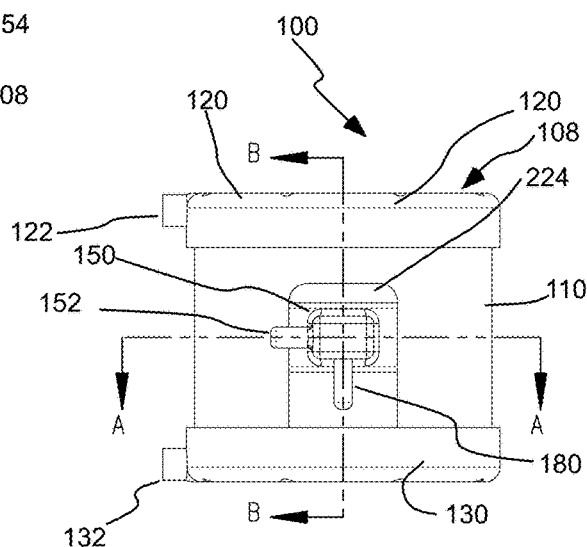
FIG. 2B illustrates a side view of the lung assist device.
Figure 2C:
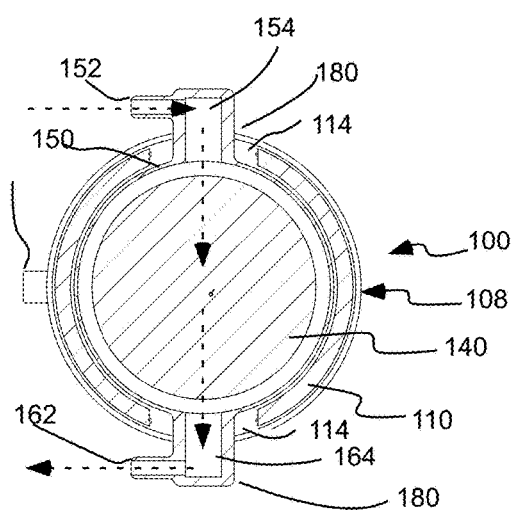
FIG. 2C illustrates a cross-sectional view (section A-A as illustrated in FIG. 2B) of the lung assist device.
Figure 2A:
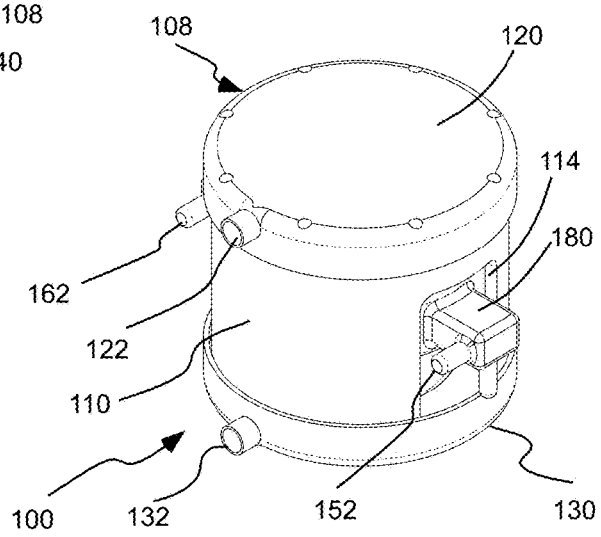
FIG. 2A illustrates a perspective view the lung assist device of FIG. 1A.
Figure 3:
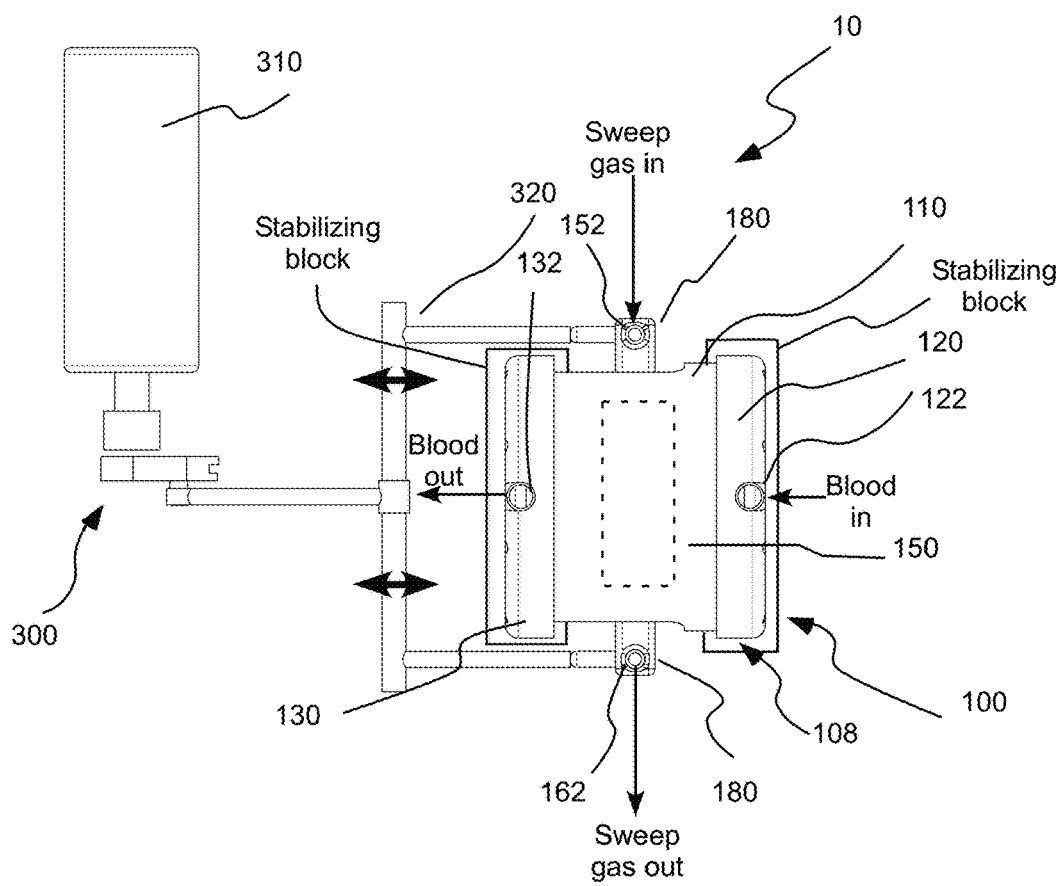
FIG. 3 illustrates a top view of a laboratory setup of the system of FIG. 1A used in representative studies hereof.

Arrows in FIG. 2D indicate the bulk direction of blood flow through device 100. Filled arrows indicate blood poor in oxygen and high in carbon dioxide content flowing into device 100 and through fiber bundle 140. Unfilled arrows indicate blood rich in oxygen and low in carbon dioxide flowing out of device 100. The gas flow path through device 100 is indicated by the dashed or broken arrows in FIG. 2C. The gas (from a source of gas or sweep gas) flows in through inlet 152 to an inlet manifold 154, which is in fluid connection with the inlet opening to the lumens of the fibers of fiber bundle 140, then across the fibers of fiber bundle 140 to an outlet manifold 164, which is in fluid connection with the outlet opening of the lumens of the fibers, and then to outlet 162. The potting of hollow fiber membrane of a fiber bundle to be in fluid connection with inlet and outlet manifolds is discussed, for example, in PCT International Patent Publication WO2014/085620, the disclosure of which is incorporated herein by reference. Gas inlet manifold 154 and gas outlet manifold 164 are sealed from contact with blood or other liquid flowing through housing.

In the illustrated embodiment, bundle 140 is carried within a movable fiber bundle carriage or fiber bundle housing 150, which includes or is connected to actuator couplings 180. Fiber bundle housing 150 contains fiber bundle 140 and couples fiber bundle 140 to a mechanical actuator via actuator couplings 180, which oscillates fiber bundle housing 150 and fiber bundle 140 therein when the actuator oscillates. Openings 151 (see FIG. 1F) in fiber bundle housing or carriage 150 provide for blood flow through fiber bundle 140. In the illustrated embodiment, inlet 152 and inlet manifold 154 are formed as a part of fiber bundle housing 150. Likewise, outlet 162 and outlet manifold 164 are formed as a part of fiber bundle housing 150. Thus, fiber bundle housing 150 further operates to deliver a sweep gas (for example, including or consisting of oxygen) to fiber bundle 140 as described above.

Actuator couplings 180 operatively connect with the remainder of fiber bundle housing 150 through first or central section 110 of housing 108 via openings 114 therein. Actuator coupling 180 is coupled with or connected to a drive mechanism including, for example, scotch-yoke mechanism 300. As known in the mechanical arts, scotch yoke mechanism 300 is a reciprocating motion mechanism which converts rotational motion to linear motion (and vice versa). In the illustrated embodiment, scotch yoke mechanism 300 is used to generate oscillatory, forward and backward motion in the direction of longitudinal axis A of device 100 as indicated by the dashed arrow in FIG. 2D (as motor 310 spins in the direction of the arrow in FIG. 1C). Scotch yoke mechanism 300 is coupled to fiber bundle 140 via a linking member 320, which is attached to actuator coupling 180 and, thereby, to carriage/housing 150. Oscillatory, linear motion is thereby translated to the fibers of fiber bundle 140, which oscillates during operation in the direction parallel to blood flow through fiber bundle 140. When blood flows through device 100, the motion of the fibers of fiber bundle 140 disrupts the concentration boundary layer of fluid forming on each fiber surface. The disruption of the concentration boundary layer increases gas exchange efficiency by speeding up the process of diffusion across the fibers in fiber bundle 140. Without limitation to any mechanism, because the Womersley number (as defined below) is relatively low (see, for example, FIG. 10), the oscillation may not significantly affect the fluid velocity boundary layer surrounding each fiber. However, the oscillation significantly affects the concentration boundary layer. In steady flow, the concentration boundary layer is the region where diffusion perpendicular to fiber surface balances convection parallel to fiber surfaces. The unsteadiness resulting from oscillation of fiber bundle 140 creates unbalance and thus disrupts the size of the concentration boundary layer and enhances mass transfer In a number of studies, a flexible and blood impermeable membrane such as a flexible bellows 190 (illustrated in FIG. 2D) contains the blood within the housing of device 10. The flexibility of bellows 190 allows unhindered motion of fiber bundle housing 150 and fiber bundle 140 while sealing blood within the device.

Scotch yoke mechanism 300 was used in the illustrated benchtop system for representative studies hereof to provide control over oscillations of fiber bundle 140. Scotch yoke mechanism 300 may not, however, be suitable for use in a clinical setting. In a clinical setting, it may desirable for the mechanism for inducing oscillation of the fiber bundle to be compact and simple in function. Oscillatory motion may, for example, be effected via a number of mechanisms including, for example, a linear actuator, a pneumatic drive, a piezoelectric actuator or a magnetically driven actuator. Each of these actuator mechanisms may, for example, replace scotch yoke 300 and directly couple to the bundle housing. Further, such actuator mechanism may be integrated within the device inlet and outlet housings as well.

In a number of studied embodiments, fiber bundle 140 had a surface area of 0.3 $m^2$ and was manufactured using commercial Oxyplus® polymethylpentene (PMP) fibers (available from Membrana GmbH of Wuppertal, Germany). Fiber bundle 140 was mounted in fiber bundle housing 150, which was formed from an acrylic polymer. Surface areas for oxygenation devices are typically upwards of 0.8 $m^2$, while surface areas for low-flow $CO_2$ removal devices, are upwards of 0.6 $m^2$. Device 100 was tested with a surface area of 0.3 $m^2$ in expectation of substantial enhancement in mass transfer (>100% from baseline). A surface area less than 0.3 $m^2$ or more than 0.6 $m^2$ may be required in some embodiments depending on the enhancement in mass transfer to fully meet $CO_2$ removal requirements as well as oxygenation requirements. In a number of embodiments, sufficient oxygenation may be achieved at normal blood flowrates in the range of approximately 2 to 3.5 Liters Per Minute (LPM) or sufficient low blood flow $CO_2$ removal (250-500 ml/min) with membrane surface area between approximately 0.3 and 0.6 $m^2$.

Figures 1D, 1E, 1F:
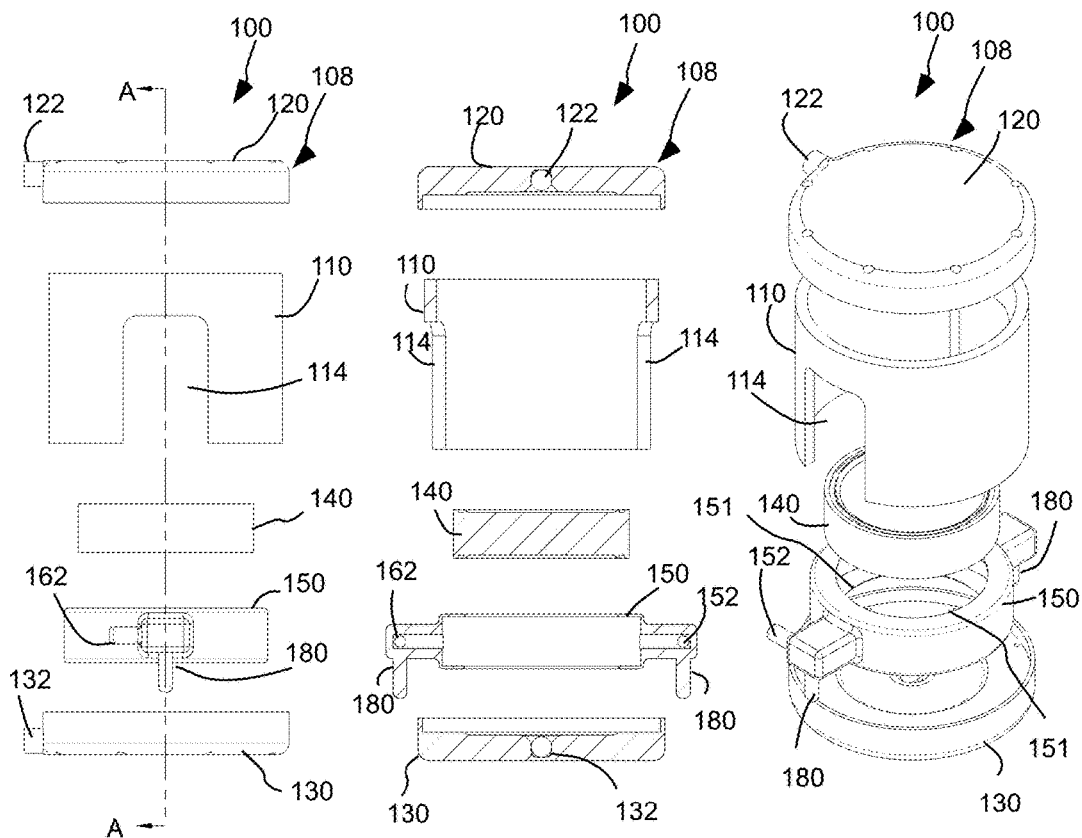
FIG. 1D illustrates a perspective exploded or disassembled view of the system of FIG. 1A.
FIG. 1E illustrates a side, cross-sectional exploded or disassembled view (section A-A of FIG. 1D) of the system of FIG. 1A.
FIG. 1F illustrates a perspective exploded or disassembled view of the system of FIG. 1A.
Figure 1G:
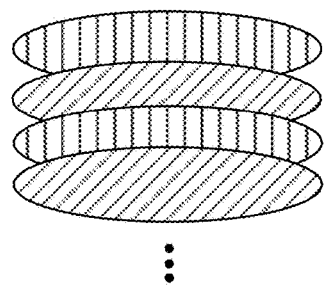
FIG. 1G illustrates an exploded view of an embodiment of a generally cylindrical fiber bundle hereof wherein the fiber bundle is formed from a plurality layers of fiber fabric and adjacent layers of fiber fabric are rotated relative to each other such that the orientation of the plurality of hollow gas permeable fibers in adjacent layers of fiber fabric are of a different orientation.

In a number of embodiments, fiber bundle 140 was a generally cylindrical bundle of hollow fiber membranes stacked in layers at, for example, 5-15 degree angles to one another and aligned generally perpendicular to the principal direction of blood flow (that is, generally perpendicular to axis A) to enhance or maximize gas exchange (see FIG. 1E). In a number of representative studied embodiments, fiber bundle 140 was a generally cylindrical bundle of hollow fiber membranes stacked in layers at approximately 7 degree angles to one another. The ends of the hollow fibers were potted into the gas manifolds (gas inlet manifold 154 and gas outlet manifold 164), into which the lumens of the fibers of fiber bundle opened.

Scotch yoke mechanism 300 provided for control of the oscillation frequency as well as amplitude. In a number of studies, $CO_2$ removal in water was used to evaluate the effect of fiber oscillation on gas transfer while running pure oxygen gas through the HFMs of fiber bundle 140. Loop temperature was controlled and maintained at 37° C. Inlet partial pressure of $CO_2$ ($pCO_2$) was maintained at 45 mmHg±5, and flowrate was maintained at 3.5 L/min. Oscillation frequencies between 0 and 50 Hz were tested and oscillation amplitudes between 0.5 and 12 mm were tested in a number of representative studies. Flowrates were measured using a Transonic T110 flow meter, and $pCO_2$ was measured using a Siemens RapidLab 248 blood gas analyzer. $CO_2$ removal was measured by analyzing $CO_2$ content in the gas exiting device 100 using a $CO_2$ analyzer (a WMA-5 $CO_2$ analyzer available from PP Systems of Amesbury, Mass.).

Figure 4:
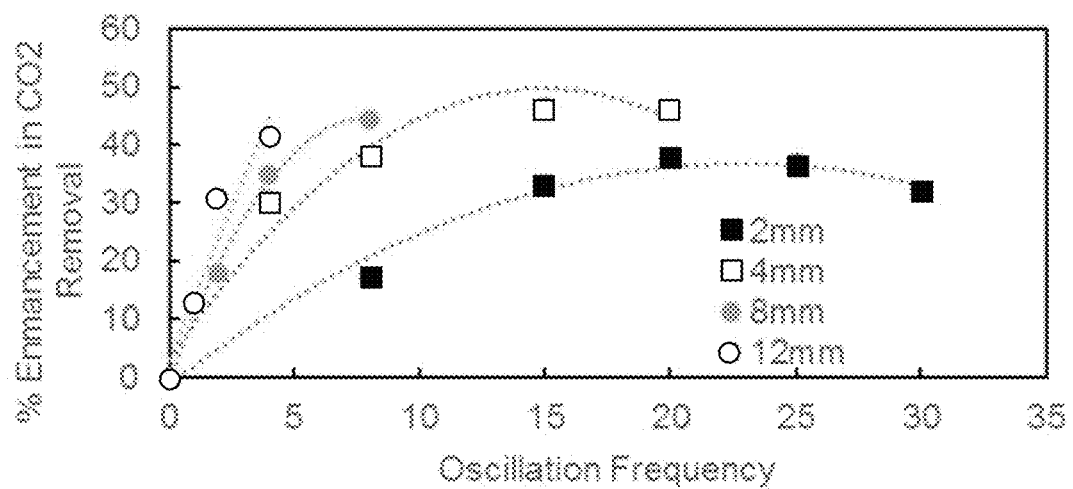
FIG. 4 illustrates a graph of studies of removal of $CO_2$ from water at various oscillation frequencies and amplitudes.

FIG. 4 illustrates representative studies of the percent enhancement of $CO_2$ removal from water. Enhancements up to 46% above baseline were achieved. The $CO_2$ removal at baseline (no motion) was 38.2 ml/min±2.52. High amplitudes and low frequencies provided similar levels of enhancement as high frequencies and low amplitudes. Gas exchange enhancement in blood would be even more substantial as gas transfer in blood is typically 2-3 times that in water. Analytically, shear stresses in the fiber bundle were estimated to be within the range of 10 N/m² and 95 N/m². These are an order of magnitude below the threshold of shear stress that could cause hemolysis.

Figure 5:
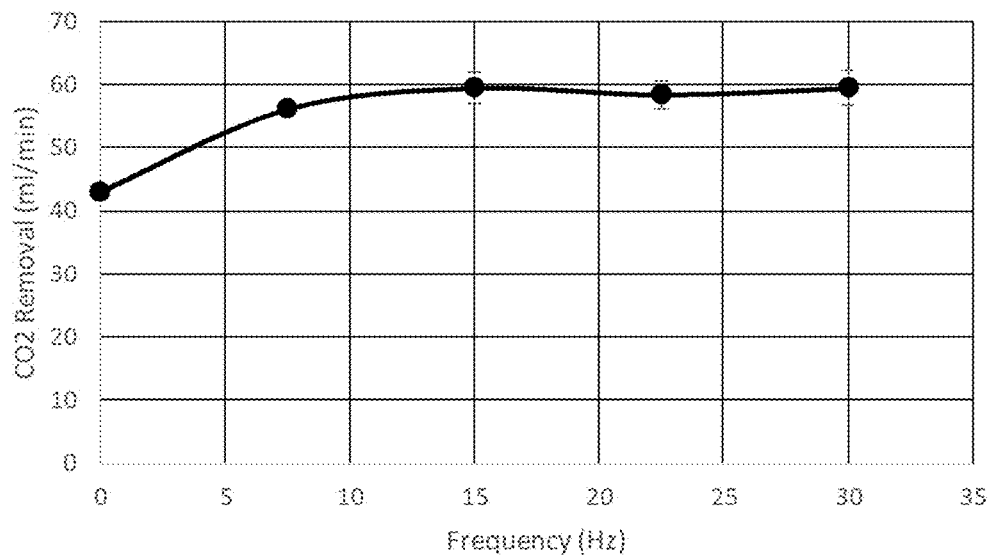
FIG. 5 illustrates in vitro removal of $CO_2$ from blood at various frequencies.
Figure 6:
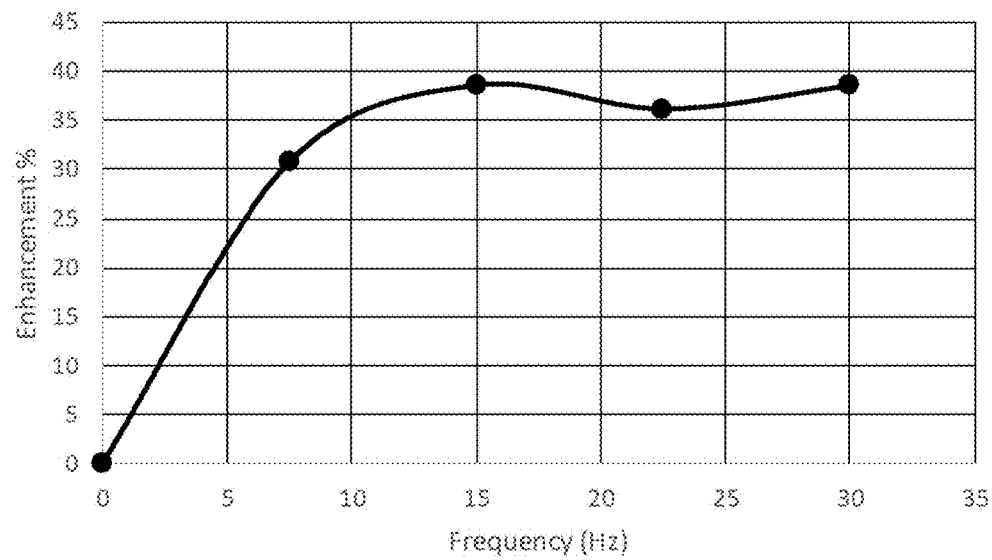
FIG. 6 illustrates in vitro enhancement of $CO_2$ removal (compared to a baseline of no motion of the fiber bundle) in blood at various frequencies.

Other representative studies of system 10 were performed wherein device 100 was tested as a low-flow (400 ml/min) $CO_2$ removal device in blood. $CO_2$ removal was tested in vitro in bovine blood in accordance with ASTM standards. Up to 60 ml/min of removal was achieved at an efficiency of 200 ml/min/m² (FIG. 5), and up to 40% enhancement from baseline as a result of the oscillations was achieved (FIG. 6). Oscillations of 2 mm were tested up to a frequency of 50 Hz.

Further blood testing was preformed following published standards and using locally collected slaughterhouse porcine or bovine blood. See ISO 7199:2009 Cardiovascular implants and artificial organs—Blood-gas exchangers (oxygenators):, 2009; ASTM F1841-97 Standard Practice for Assessment of Hemolysis in Continuous Flow Blood Pumps:, 2013; and Koller T, Hawrylenko A: Contribution to the in vitro testing of pumps for extracorporeal circulation *J Thorac Cardiovasc Surg* 54: 22-29, 1967. Oxygenation was characterized in a single pass loop system in which blood was conditioned to have an oxygen saturation of 65%±5% and a $pCO_2$ of 45 mmHg±5 mmHg. Pure oxygen sweep gas flowed through the device. Two fiber bundles were characterized, a 0.1 m² cross-sectional area test module and a 0.3 m² cross-sectional area scaled-up module. The test module was characterized at 1 L/min blood flow and the scaled-up module was tested at 3.5 L/min blood flow. Stroke length was varied between 4 mm and 16 mm while frequency was varied between 0 Hz and 30 Hz.

Hemolysis was characterized in a continuous flow loop system using an 800 mL compliant blood reservoir available from Medtronic of Minneapolis, Minn. The loop included the test module and a BIO-MEDICUS® blood pump available from Medtronic. Based on gas exchange results, three stroke length/frequency conditions were tested (4 mm/15 Hz, 8 mm/10 Hz, 16 mm/7 Hz). Each condition was tested for 2 hours. Plasma free hemoglobin versus time was measured and a normalized index of hemolysis (NIH) was calculated to represent the level of hemolysis in each loop.

Figure 7A:
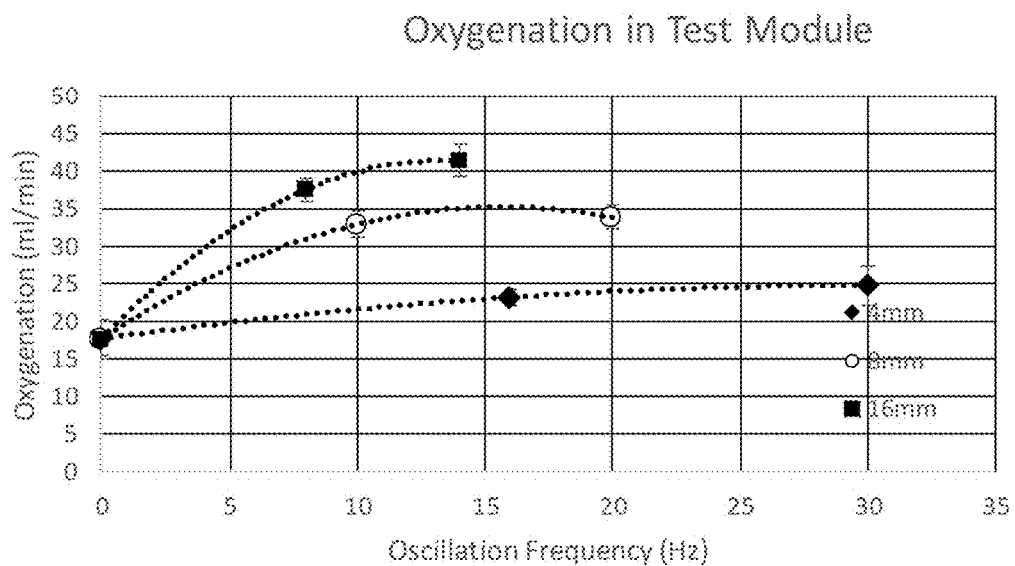
FIG. 7A illustrates in vitro oxygenation of blood at various frequencies in a test module.
Figure 7B:
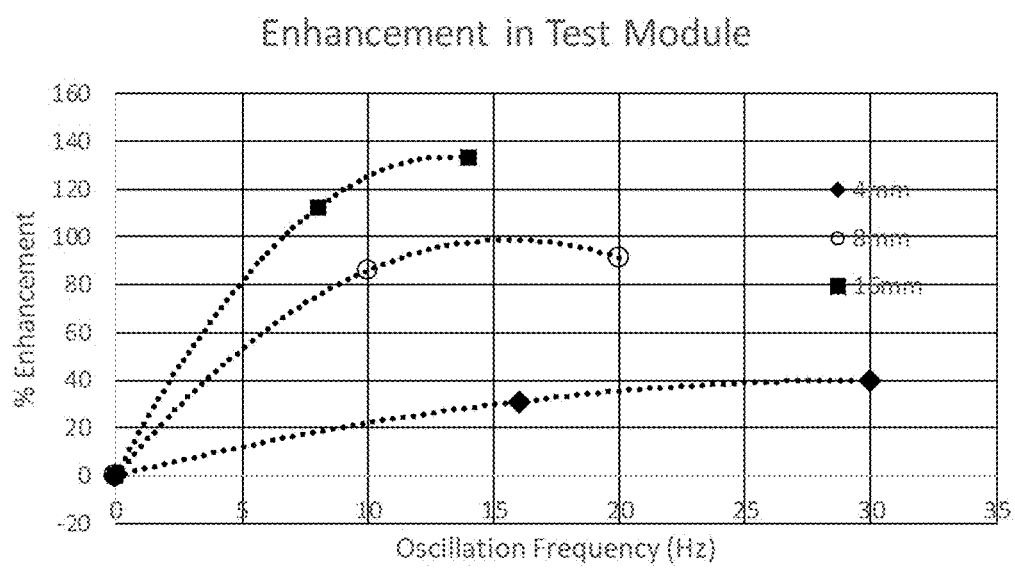
FIG. 7B illustrates in vitro enhancement of oxygenation (compared to a baseline of no motion of the fiber bundle) in blood at various frequencies in a test module.
Figure 8A:
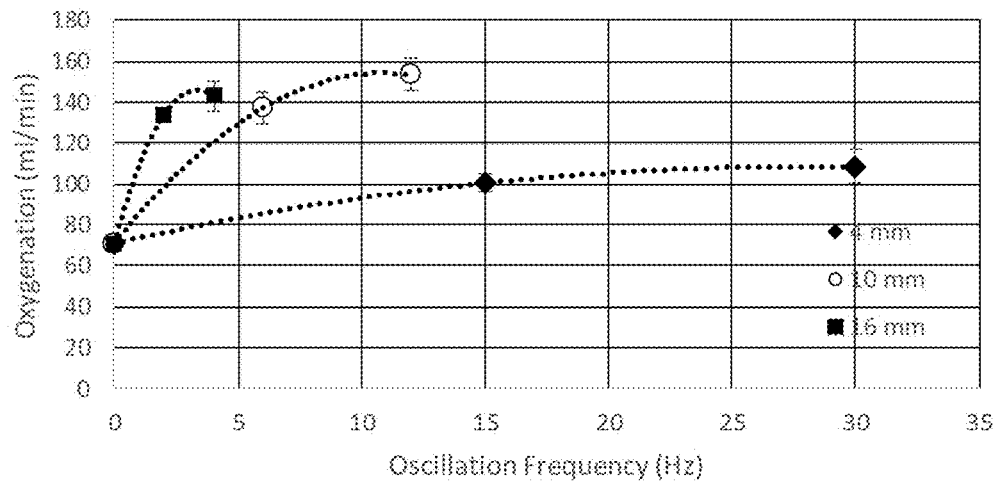
FIG. 8A illustrates in vitro oxygenation of blood at various frequencies in a scaled-up module.
Figure 8B:
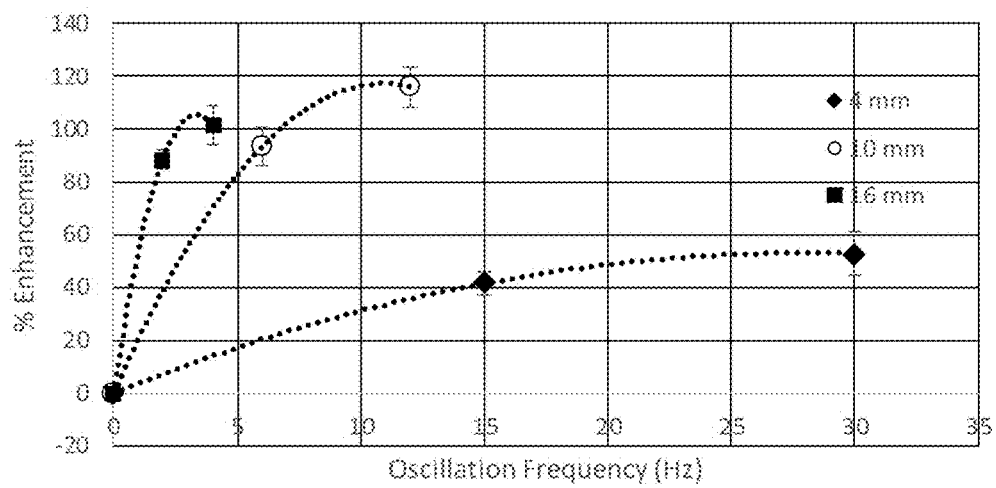
FIG. 8B illustrates in vitro enhancement of oxidation (compared to a baseline of no motion of the fiber bundle) in blood at various frequencies in a scaled-up module.

FIGS. 7A and 7B illustrate that baseline oxygenation in the test module (17.7 ml/min) was increased over 120% above baseline in the presence of oscillations to greater than 40 ml/min. When scaled up, baseline oxygenation (71.0 ml/min) increased up to 116% to greater than 150 ml/min as shown in FIGS. 8A and 8B. The efficiency of the scaled-up module is over 500 ml/min/m², which is higher than published results for other devices clinically used or in research development. The, non-optimized scaled-up device meets approximately 70% of the need for oxygenation in adults (200 ml/min).

Figure 9:
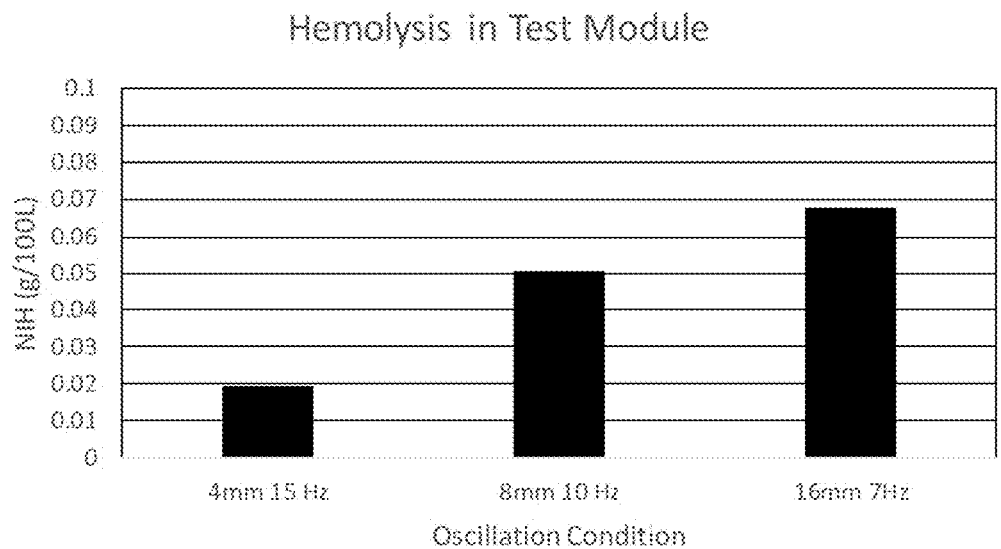
FIG. 9 illustrates a study of hemolysis at several combinations of oscillation amplitude and frequency.

An initial hemolysis experiment on the test module (FIG. 9) indicates hemolysis in the presence of oscillations under the conditions tested. Moderate hemolysis (0.067 g/100 L) is present as oscillations are created. This hemolysis is likely a result of mechanical components of the device rather than the oscillations, based on shear stress estimations. Hemolysis is acceptable (based upon a threshold level of NIH of 0.05 g/100 L) for conditions of 8 mm/10 Hz and 4 mm/15 Hz. At these oscillation conditions, gas exchange is enhanced over 80% from baseline with a high efficiency of 320 ml/min/m².

Efficiency may thus be significantly improved at acceptable levels of hemolysis in the systems, devices and method hereof. The representative systems, devices and methods studied herein were not optimized. Further optimization of device components and operational methodologies (including, for example, device component shapes and/or dimensions, fiber bundle shapes and/or dimensions, fiber bundle surface area, oscillation characteristics, flow characteristics etc.) may, for example, reduce hemolysis and increase oxygenation to 100% of needs.

Mass transport over an array of cylinders such as the fibers of fiber bundle 140 in pulsatile flow is provided by equation (1) below:

$$\alpha^2 Sc \frac{\partial C}{\partial t} + Re\ Sc\ \nabla \cdot (uC) = \nabla^2 C \qquad (1)$$

The conservation of mass and momentum equations can be simplified and are represented in dimensionless form as shown below. In equation (1), $\alpha$ is the Womersley number, Sc the Schmidt number, Re the Reynold's number and C the concentration of the gas being added or removed from the fluid/blood. Thus, these are two separate approaches to enhance mass transfer. In stationary mixing devices mass transfer can be improved by increasing Re. This result can be achieved by increasing velocity of flow past the fiber. In this approach, $\alpha$ is 0. Another approach, which is taken in the systems, devices and methods hereof, is to add the $\alpha$ component through oscillating fibers. The oscillation of the fibers causes $\alpha$ to be non-zero, as a transient inertial force term is added.

$$\alpha = \left(\frac{\text{Transient Inertial Force}}{\text{Viscous Force}}\right)^{\frac{1}{2}};$$

$$\alpha = \left(\frac{\rho\omega \overline{V}_f}{\mu V_o/k}\right)^{\frac{1}{2}};$$

$$V_f \approx V_o, \alpha = \left(\frac{\rho\omega}{\mu/k}\right)^{\frac{1}{2}};$$

wherein α is the Womersley Number, ρ is fluid density, ω is Oscillation Frequency, $V_f$ is fiber velocity, $V_o$ is fluid velocity, μ is dynamic viscosity, and k is Darcy Permeability.

Figure 10:
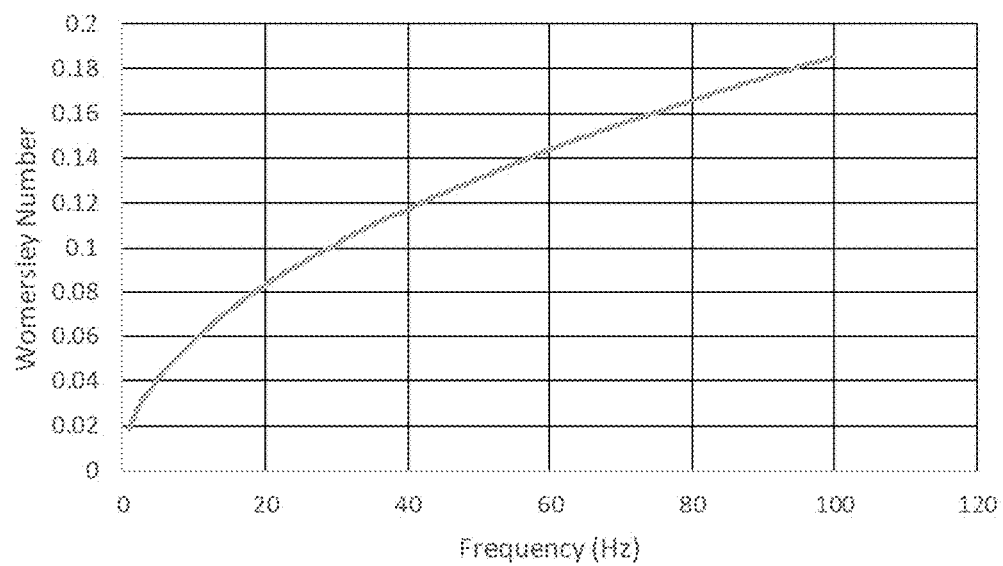
FIG. 10 illustrates Womersley number as a function of oscillation frequency.

Though the Womersley number is small as a result of the large viscous force of the blood past the fibers, addition of this term causes a relatively large effect because the product of the Womersley number and the Schmidt number (μ/ρD, wherein D mass diffusivity, which is in the range of approximately 1200-3000) is still large. As shown in FIG. 10, small frequencies of up to 30 Hz increase the Womersley number substantially (slope of 0.0050/Hz) whereas higher frequencies of 30 Hz-100 Hz have a slope of 0.0014/Hz. Thus, testing has been primarily focused in the 0-30 Hz range. Additionally, mechanical constrains in studied embodiments limited frequencies to an absolute maximum of 100 Hz. The oscillatory motion in this analysis is not sensitive to direction of flow, i.e. applicable to axial as well as torsional oscillations. Oscillation amplitudes between 2 mm and 16 mm were feasible in a number of embodiments of the studied systems and devices hereof. However, a tradeoff between operable frequency and amplitude was seen in such systems. At higher amplitudes, testable frequencies are lower as a result of the viscous force of the blood on the fibers. In a number of embodiments, ranges of operation for any mode of oscillation are such that the Womersley number is in the range of approximately 0.05 to 0.25 and the frequency is in the range of approximately 1 to 100 Hz, or approximately 1 to 30 Hz. For rotational motion, rather than an amplitude, relative movement of fibers may be considered. For a disc-shaped, stacked bundle as described herein, a maximum of 16 mm of circumferential motion at the outer diameter of the fiber bundle occurs in a number of embodiments hereof. In a number of embodiments, the product of Womersley number and the Schmidt number (α*Sc) is 10 or greater. From a dimensional analysis point of view, such values of α*Sc provide the potential to alter the normal concentration boundary layers from those for steady flow.

In the embodiments discussed above, an axial oscillatory motion was used to disrupt the boundary layer surrounding the fibers of the fiber bundle. However, other types of oscillatory motion may be used (either alone or in combination). For example, the fiber bundle may be torsionally oscillated (that is, oscillated over a range of degrees about the axis thereof).

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. An extracorporeal system for lung assist comprising:
a system housing, the system housing comprising a blood flow inlet and a blood flow outlet;
a fiber bundle housing movably positioned within the system housing, the fiber bundle housing comprising a gas inlet and a gas outlet;
a fiber bundle in operative connection with the fiber bundle housing, the fiber bundle comprising a plurality of hollow gas permeable fibers, wherein lumens of the plurality of hollow gas fibers are in fluid connection with the gas inlet at a first end thereof and in fluid connection with the gas outlet as a second end thereof;
an actuator to impart linear oscillatory motion to the fiber bundle housing and thereby to the fiber bundle.

2. The extracorporeal system of claim 1 wherein the plurality of hollow gas permeable fibers are adapted to permit diffusion of gas between blood and an interior of the plurality of hollow gas permeable fibers, the plurality of hollow gas permeable fibers being positioned such that blood flows around the plurality of hollow gas permeable fibers when flowing through the fiber bundle, and the plurality of hollow gas permeable fibers extending generally perpendicular to the direction of bulk flow of blood through the fiber bundle.

3. The system of claim 1 wherein the system is a paracorporeal system.

4. The system of claim 1 wherein the plurality of hollow gas permeable fibers comprise a plurality of layers of fiber fabric, each of the plurality of layers of fiber fabric comprising hollow gas permeable fibers.

5. The system of claim 4 wherein adjacent layers of fiber fabric are rotated relative to each other such that the orientation of the plurality of hollow gas permeable fibers in adjacent layers of fiber fabric are of a different orientation.

6. The system of claim 1 wherein blood is blocked from flowing to the gas inlet and the gas outlet.

7. The system of claim 1 wherein the plurality of hollow gas permeable fibers is formed in at least one generally cylindrical fiber bundle.

8. The system of claim 7 wherein a mean velocity of blood through the fiber bundle is in the range of approximately 0.6 to 7 cm/sec for a high flow oxygenation mode of operation and in the range of approximately 0.08 to 1.2 cm/sec for a low flow $CO_2$ removal mode of operation.

9. The system of claim 7 wherein a cross-sectional area of the fiber bundle is no more than 0.6 m².

10. The system of claim 7 wherein the system is adapted to deliver blood flows in the range of approximately 2 to 4 liters per minute for a high flow oxygenation mode of operation and blood flows in the range of approximately 250 to 400 ml/min for a low flow $CO_2$ removal mode of operation.

11. The system of claim 10 wherein the flow is adjustable.

12. The system of claim 1 wherein the system housing comprises a plurality of openings via which the fiber bundle housing is coupled to the actuator.

13. The system of claim 1 wherein a product of Womersley number α, wherein $$\alpha = \left(\frac{\rho\omega \overline{V}_f}{\mu V_o/k}\right)^{\frac{1}{2}},$$

and the Schmidt number Sc, wherein $$Sc = \mu/\rho D$$

is at least 10, wherein ρ is fluid density, ω is Oscillation Frequency, $V_f$ is fiber velocity, $V_o$ is fluid velocity, μ is dynamic viscosity, k is darcy permeability and D is mass diffusivity.

14. A method of providing lung assist, comprising:

providing a system comprising a system housing, the system housing comprising a blood flow inlet and a blood flow outlet in fluid connection with a patient's vasculature, a fiber bundle housing movably positioned within the system housing, the fiber bundle housing comprising a gas inlet and a gas outlet, and a fiber bundle in operative connection with the fiber bundle housing, the fiber bundle comprising a plurality of hollow gas permeable fibers, wherein lumens of the plurality of hollow gas fibers are in fluid connection with the gas inlet at a first end thereof and in fluid connection with the gas outlet as a second end thereof; and imparting linear oscillatory motion to the fiber bundle housing and thereby to the fiber bundle.

15. The method of claim 14 wherein a product of Womersley number α wherein $$\alpha = \left(\frac{\rho \omega \overline{V}_f}{\mu V_o / k}\right)^{\frac{1}{2}},$$

and the Schmidt number Sc wherein $$Sc = \mu / \rho D$$

is at least 10, wherein ρ is fluid density, ω is Oscillation Frequency, $V_f$ is fiber velocity, $V_o$ is fluid velocity, μ is dynamic viscosity, k is darcy permeability and D is mass diffusivity.

16. The method of claim 14 wherein the plurality of hollow gas permeable fibers is formed in at least one generally cylindrical fiber bundle.

17. The method of claim 16 wherein a mean velocity of blood through the fiber bundle is in the range of approximately 0.6 to 7 cm/sec for a high flow oxygenation mode of operation and in the range of approximately 0.08 to 1.2 cm/sec for a low flow $CO_2$ removal mode of operation.

18. The method of claim 16 wherein a cross-sectional area of the fiber bundle is no more than 0.6 $m^2$.

19. The method of claim 16 wherein the system is adapted to deliver blood flows in the range of approximately 2 to 4 liters per minute for a high flow oxygenation mode of operation and blood flows in the range of approximately 250 to 400 ml/min for a low flow $CO_2$ removal mode of operation.

20. The method of claim 19 wherein the blood flow is adjustable.

21. The method of claim 16 wherein the system housing comprises a plurality of opening via which the fiber bundle housing is coupled to the actuator.

22. An extracorporeal system for lung assist system, comprising: a system housing, a generally cylindrical fiber bundle movably positioned within the system housing and comprising a plurality of hollow gas permeable fibers, and an actuator to impart linear oscillatory motion to the fiber bundle.

* * * * *

UNITED STATES PATENT AND TRADEMARK OFFICE
CERTIFICATE OF CORRECTION

PATENT NO. : 10,335,530 B2
APPLICATION NO. : 15/288111
DATED : July 2, 2019
INVENTOR(S) : Shalv Madhani, Brian Joseph Frankowski and William J. Federspiel It is certified that error appears in the above-identified patent and that said Letters Patent is hereby corrected as shown below:

On the Title Page
Item (57) In the Abstract
Line 10, delete "the gas outlet as a second" and insert -- the gas outlet at a second --.
In the Claims
Column 10, Claim 1, Line 9, delete "the gas outlet as a second" and insert -- the gas outlet at a second --.
Column 11, Claim 14, Line 17, delete "the gas outlet as a second" and insert -- the gas outlet at a second --.

Signed and Sealed this
Twelfth Day of November, 2019

Andrei Iancu
*Director of the United States Patent and Trademark Office*